United States Patent
Hengerer

(10) Patent No.: US 7,713,516 B2
(45) Date of Patent: May 11, 2010

(54) METHOD FOR DETERMINING SUITABILITY OF VARIOUS CONTRAST AGENTS FOR THE IMAGING EXAMINATION OF THE PATIENT AND USES OF THE LIGAND CONTAINED IN A SELECTED CONTRAST AGENT

(75) Inventor: Arne Hengerer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1177 days.

(21) Appl. No.: 11/305,003

(22) Filed: Dec. 19, 2005

(65) Prior Publication Data

US 2006/0133995 A1 Jun. 22, 2006

(30) Foreign Application Priority Data

Dec. 20, 2004 (DE) ................ 10 2004 061 348

(51) Int. Cl.
*A61B 5/055* (2006.01)
*A61K 49/04* (2006.01)

(52) U.S. Cl. .......................... 424/9.3; 424/9.4
(58) Field of Classification Search .................. 424/9.3, 424/9.4
See application file for complete search history.

(56) References Cited

FOREIGN PATENT DOCUMENTS

| DE | 20 2004 012 479 U1 | 9/2004 |
|----|--------------------|--------|
| WO | WO 99/56787 | 11/1999 |
| WO | WO 99/56788 | 11/1999 |

OTHER PUBLICATIONS

King C.P. Li et al., <<Combined vascular targeted imaging and therapy : a paradigm for personalized treatment>>, Journal of Cellular Biochemistry, ISSN 1097-4644, 2002, Supplement 39, 65-71.
Dr. A. Hengerer et al. Siemens AG, Medical Solutions, Erl. Germany: "Molecular Biology for Medical Imaging", electromedica 69 (2001) No. 1.
D. Högemann et al. "High Throughput Magnetic Resonance Imaging for Evaluating Targeted Nanoparticle Probes", Bioconjugate Chem. 2002, 13, 116-121.
Willibald Pschyrembel: "Kllinisches Wörterbuch", 259. neu bearb. Auflage, Berlin: Walter de Gruyter GmbH & Co. KG, 2002, p. 207, ISBN: 3-11-016522-8 [Translation: Pschyrembel Clinical Dictionary, 259., new and revised edition—Berlin: de Gruyter, 2002, p. 207, ISBN 3-11-0116522-8].
German Office Action dated Oct. 23, 2006 for counterpart German Application No. 10 2004 061 348.6.

*Primary Examiner*—Raymond J Henley, III
(74) *Attorney, Agent, or Firm*—Harness, Dickey & Pierce, P.L.C.

(57) ABSTRACT

A method is for determining suitability of various contrast agents for the imaging examination of the. In this case, a tissue sample is taken from the patient, it is divided into a plurality of individual samples and a contrast agent which binds to a particular target structure in the tissue is added to each individual sample. The individual samples are examined by an analysis or imaging method in order to determine the suitability of the various contrast agents for the imaging examination of the patient.

24 Claims, 2 Drawing Sheets

METHOD FOR DETERMINING SUITABILITY OF VARIOUS CONTRAST AGENTS FOR THE IMAGING EXAMINATION OF THE PATIENT AND USES OF THE LIGAND CONTAINED IN A SELECTED CONTRAST AGENT

The present application hereby claims priority under 35 U.S.C. §119 on German patent application number DE 10 2004 061 348.6 filed Dec. 20, 2004, the entire contents of which is hereby incorporated herein by reference.

FIELD

The present invention generally relates to a method for the determination and/or potentially eventual selection of a suitable contrast agent for carrying out an imaging examination of a patient, and/or to the use of a ligand contained in the selected contrast agent as a pharmaceutical active agent for treating the patient, as a carrier for a pharmaceutical active agent, as a ligand of a further contrast agent and/or as an "in vitro" diagnostic reagent.

BACKGROUND

Conventional imaging diagnosis, for example X-ray computer tomography (CT), magnetic resonance tomography (MRT), positron emission tomography (PET), single photon emission computed tomography (SPECT) or optical imaging such as NIRF (Near Infra Red Fluorescence) provides anatomical or functional physiological information about the body. In this case, contrast agents are often used to make pathological tissue visible via physiological parameters such as blood supply or tissue density.

In PET, for example, biomolecules in which a stable isotope is replaced by a positron emitter, for example $^{11}$C, $^{13}$N or $^{15}$O, are used as contrast agents (CA). In this way, it is possible to monitor the metabolic behavior of the labeled biomolecules. Paramagnetic or ferromagnetic substances, for example chelated Gd or iron oxide nanoparticles, are used in MRT as contrast agents which can accumulate on further molecules for functionalization. These contrast agents concentrate, for example, in tissues which may be pathologically modified, where they lead to contrast changes in the image.

Currently approved contrast agents, however, are not very specific. Concentration of the MRT contrast agent Gd-DOTA in the brain may, for example, be caused by a tumor, a stroke, an MS lesion or any other physiological modification which affects the blood-brain barrier.

More recent so-called molecular imaging (MI) contrast agents allow very much more specific characterization of pathological tissues by the aforementioned imaging methods (see A. Hengerer, T. Mertelmeier, Siemens AG, Medical Solutions, Erlangen, Germany: "Molecular Biology for Medical Imaging" electromedica 69 (2001) no. 1).

Molecular imaging integrates molecular biological methods, for example antigen-antibody interactions or peptide receptor binding, and imaging technologies. In this way, non-invasive characterization of biological processes is possible at the cellular or molecular level. Molecular imaging thus involves the in vivo visualization of defective metabolic processes by biological reagents (molecular imaging contrast agents) which bind to molecular disease markers or target structures in the body and hence label them selectively. As a supplement to conventional imaging, molecular imaging provides complementary information about the position and—in the ideal case—the amount of molecular target structures in the living body, without the need for a biopsy.

Since pathological processes first manifest themselves at the molecular level, before (macro-) anatomical or functional expressions of the disease occur, molecular imaging allows diagnosis in the early stages of a disease.

A molecular imaging contrast agent therefore includes both a contrasting unit, for example an iron oxide nanoparticle in the case of MRI, and a molecular structure which interacts with the target structure in the tissue.

This molecular structure is also referred to as the "ligand" of the contrast agent.

WO 99/56788 discloses a method for the selection of a suitable molecular imaging contrast agent for a particular target tissue. This may be a cell culture or a tissue sample. In the method, a large number of different contrast agents are generated by the conjugation of contrasting units with a multiplicity of different ligands, for example peptides, oligomers, synthetic monomers or antibodies etc. The contrast agents are added to the target tissue and the binding affinity is tested by an analytical method.

The article by K. P. C. Li et al., "Combined vascular targeted imaging and therapy: a paradigm for personalized treatment", Journal of Cellular Biochemistry, ISSN 1097-4644, 2002, Supplement 39, 65-71, discloses a nanoparticle technology for loading particles both with ligands that bind to target structures and with contrasting units and therapeutic active agents. The nanoparticles respond, in particular, to endothelial receptors. Before treatment with a nanoparticle for administering a pharmaceutical active agent, the affinity of this nanoparticle can be tested by "in vivo" imaging after having administered a nanoparticle which is loaded with a contrasting unit but not with the therapeutic active agent.

In many applications, MI contrast agents are so specific that imaging examination cannot be carried out with the same contrast agent on every patient, even if they have the "same" initial diagnosis/suspected diagnosis. Many diseases that are currently grouped under one diagnosis (for example tumors of particular organs) actually subsume various molecular diseases with anatomically similar expression. Since the underlying pathological mechanisms are different, however, there may also be different target structures for the imaging.

In order to exploit the possibilities of specific molecular imaging contrast agents, each patient must thus undergo the same imaging method several times, with a different contrast agent in each case. If a contrast agent is selected with only one particular ligand that binds to particular molecular disease marks, then no diagnosis if is possible if the contrast agent has been selected incorrectly.

SUMMARY

It is an object of at least one embodiment of the invention to facilitate the use of such MI contrast agents for diagnosis by a method for the selection of a suitable contrast agent. It is also an object at least one embodiment to make the possibilities of molecular imaging better usable for therapy planning and therapy control.

It may achieve one or more of these objects by at least one embodiment of a method for the selection of a suitable contrast agent for carrying out an imaging examination of a patient.

The method of at least one embodiment comprises the following steps:

a tissue sample is taken from the patient;
the tissue sample is divided into a plurality of individual samples;
a contrast agent which binds to a particular target structure in the tissue is added to each individual sample;

the individual samples are examined by an examination method in order to determine the suitability of the various contrast agents for the imaging examination of the patient.

This selection process can be fully automated in a "turnkey" system. The optimal contrast agent for a particular patient, for example, may be selected in radiology from a pool of reagents. This allows highly specific visualization, localization and possibly quantification of biochemical functions and their disruption in the body. This is indispensable for many individualized therapies. The contrast agent determined in this way can be used for the imaging examination of the patient.

Preferably, the various contrast agents differ not with respect to the part that generates the actual image contrast, but with respect to a ligand bound to it, which accumulates at a particular target structure in the tissue. At least one embodiment of the invention also relates to the use of the ligand determined in this way as a pharmaceutical active agent for treating the patient. This allows extremely efficient "drug targeting", and the dose administered can be determined accurately by the imaging method.

Furthermore, according to a further aspect of at least one embodiment of the invention, the ligand which has been determined may itself be used as a pharmaceutical active agent. Examples of ligands which themselves can be used as therapeutics are antibodies, peptides or nucleic acids, which are used for example in the scope of an antisense therapy.

According to a further aspect of at least one embodiment of the invention, the ligand which has been determined may be used as a ligand of a further contrast agent for the imaging examination of the patient by another imaging method. For example, the MRT contrast particle such as an iron oxide nanoparticle may be substituted by a fluorescent dye which can be detected using optical imaging methods. Optical examinations are attractive since the method is not a burden for the patient and relatively cost-effective. When the region to be examined is limited, since the focus of the disease has already been localized, advantageous detectors with a small field of view (FoV) can be used. Nevertheless, whole-body imaging methods such as PET, SPECT or MRI are particularly suitable for the proposed selection method owing to the possibilities of three-dimensional imaging. MRT is distinguished by a high image resolution, while PET and SPECT are preferably used whenever high sensitivity is necessary.

According to yet another aspect of at least one embodiment, the ligand of the selected contrast agent is used as an "in vitro" diagnostic reagent in a consecutive examination of the patient for therapy control.

BRIEF DESCRIPTION OF THE DRAWINGS

The invention will now be explained in more detail with reference to example embodiments and the appended drawings. In the drawings.

DETAILED DESCRIPTION OF THE EXAMPLE EMBODIMENTS

Figure 1:
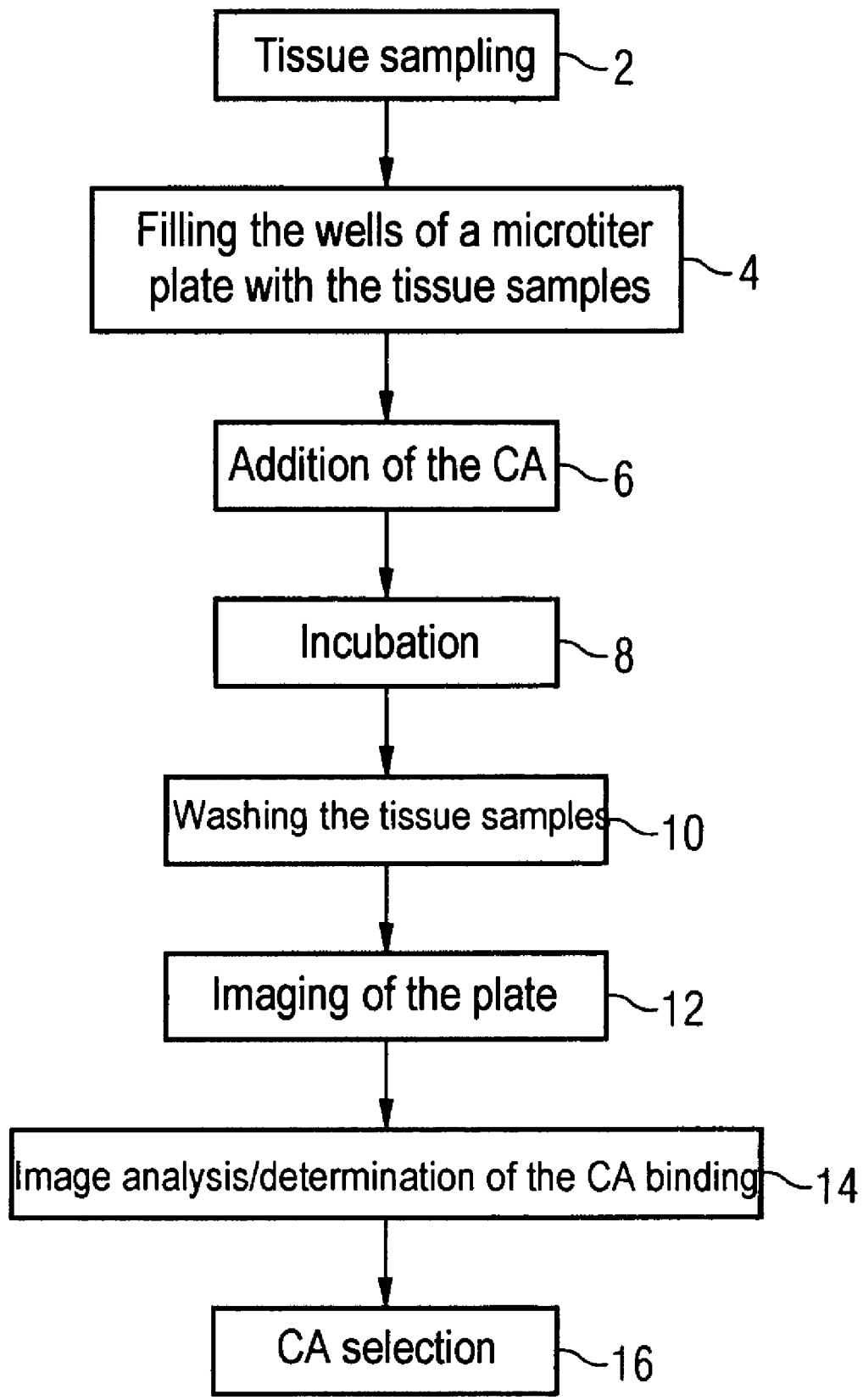
FIG. 1 shows a flow chart of an embodiment of the method according to the invention.

A tissue sample, for example a blood or biopsy sample, is first taken from the patient in step 2. It is preferable to use a tissue sample which has already been obtained in the scope of a screening examination or for "in vitro" diagnostic preliminary examinations.

The sample is then analyzed in a parallelized procedure (high throughput screening, HTS), with as many tissue samples as possible being examined at the same time. According to one embodiment of the invention, the wells of a microtiter plate are for this purpose filled with individual tissue samples, as described in the publication "High Throughput Magnetic Resonance Imaging for Evaluating Targeted Nanoparticle Probes", D. Hoegemann et al., Bioconjugate Chem. 2002, 13, 116-121. There, the contrast agent is a magnetically labeled nanoparticle to which various peptides are bound or conjugated. The disclosed content of this article is hereby incorporated into this application by reference, in its entirety.

In step 6 of the method, the various contrast agents are added to the individual samples. The contrast agents respectively contain a contrasting part, for example an iron oxide particle, which generates contrast in the imaging method being used, and a particular ligand which binds to particular target structures in the tissue. A pool of reagents, for example obtained from a peptide library, is used for the ligand.

In other embodiments of the invention, the ligand is selected from: peptide libraries, nucleic acid libraries (including antisense libraries), phage libraries, adenovirus libraries or libraries of derivative viruses or retroviruses, synthetic libraries (for example dentrimer libraries) or microbubble-based libraries (for example liposome libraries). The target structure in the tissue sample is, for example, an antigen, an enzyme or a nucleic acid.

The individual samples are incubated in step 8 with the various contrast agents, in order to achieve binding of the ligand to the target structure if the sample contains the respective target structure.

Optionally, the tissue samples are washed after the end of the incubation time, in order to remove unbound contrast agent. This is done, for example, by rinsing the samples with saline solution. It is preferable to use assays which do not require the contrast agent to be washed off.

The individual samples supplemented with the various contrast agents are then examined, preferably together, by an imaging method such as PET, SPECT, MRT or NIRF in order to determine the suitability of the various contrast agents for the imaging examination of the patient (step 12). Ideally, the concentration of the contrast agent in the respective individual sample and the binding affinity of the respective contrast agent ligand to the target structure can be deduced from the recorded image.

In the case of MRT, the imaging itself may be carried out according to the method described in the aforementioned article in Bioconjugate Chem. In this case, a plurality of microtiter plates are examined simultaneously, so that up to 1920 individual samples could be analyzed with an examination time of about 50 minutes. A measure of the T2 relaxation time is determined by varying the echo time, and the concentration of the contrast agent in the individual wells of the plate is thereby estimated. In the case of an optical imaging method, it is expedient to examine only one microtiter plate at a time.

Besides the imaging methods developed for "in vivo" diagnosis, assays conventionally employed in "in vitro" diagnosis may also be used in order to detect the binding, i.e. in order to identify the ligands which react with the patient sample. For example, fluorescence and bioluminescence examinations or other enzymatic tests may be suitable for this. It is preferable to use homogeneous assays which do not require any elaborate sample preparation and are therefore easy to automate.

The data determined in this way make it possible to select a contrast agent with a suitable ligand, which has an optimal affinity for the target structures of the tissue sample (step 16). The contrast agent to be applied during the subsequent examination is thus selected from a pool of different contrast agents, in order to ensure that it binds to the patient sample and is suitable for verifying the laboratory diagnosis or for localizing the focus of the disease. In a subsequent step (not shown in FIG. 1), the selected contrast agent is administered to the patient and the patient is examined by the respective imaging method. The imaging data obtained in this way can be used for the therapy planning.

Figure 2:
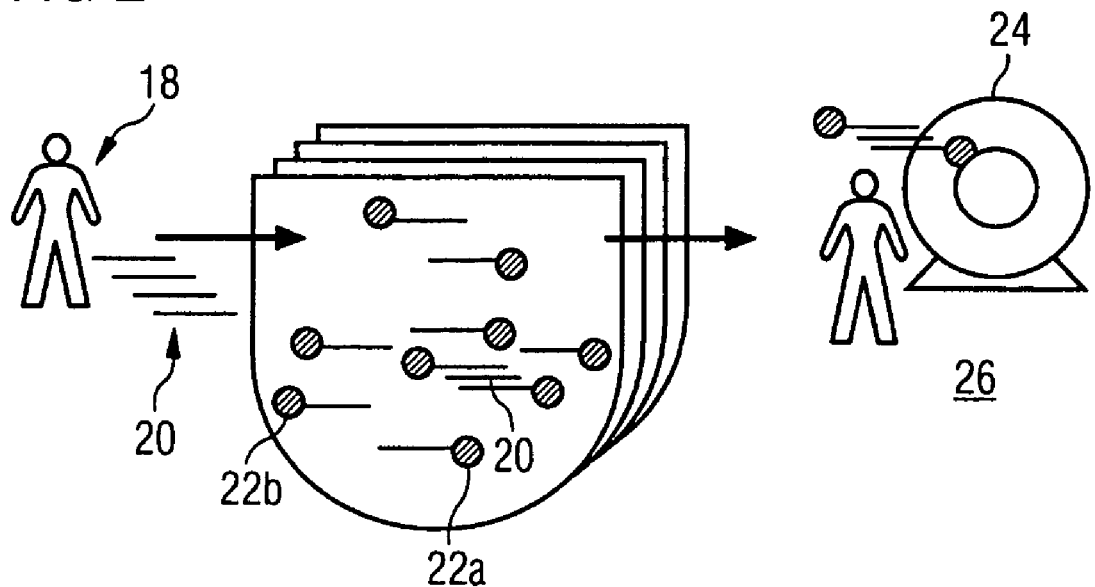
FIG. 2 shows a schematic representation of an embodiment of the method according to the invention.

The method described above is represented differently in FIG. 2. Here, the tissue sample 20 is taken from the patient 18, is subsequently mixed with the contrast agent particles 22a, 22b, and is subjected to a high throughput screening "in vitro" imaging method. The drawing schematically represents the way in which the biologically active ligands of the contrast agent particles 22a, 22b accumulate on the tissue sample 20. The contrast agent that binds best is then selected, and the patient is examined in the schematically represented MR tomograph in step 26. The contrast agent selected in the previous step is used for this.

Figure 3:
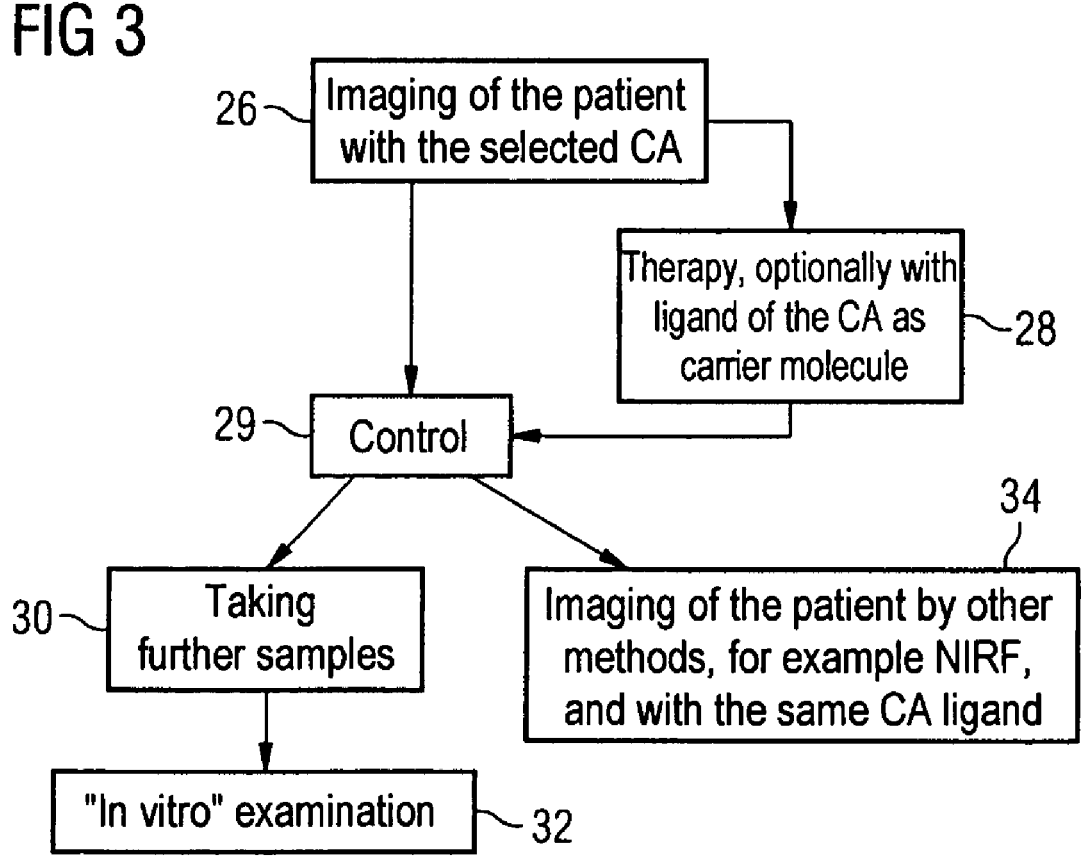
FIG. 3 shows a flow chart of the method steps for using the selected contrast agent and ligand according to the exemplary embodiment.

Nevertheless, the preferred applications of the method according to embodiments of the invention have not yet been exhausted by this. An example of further method steps is represented in FIG. 3.

After the imaging examination of the patient with the selected contrast agent, a therapy 28 such as radiation therapy or antisense gene therapy may optionally be carried out. In particular cases, the ligand of the selected contrast agent may in this case be used as a carrier molecule for therapeutics, or may itself act directly as a therapeutic. It is necessary to use therapeutic doses in this case. Dose determination can be carried out with the aid of the upstream imaging. This allows patient-specific application and accurately plannable dosing of the therapeutic active agent.

The ligand determined in step 16 may again be used for the therapy control 29.

The contrast agent may furthermore be modified by replacement of the contrasting particle, in order to be used for diagnosis in other imaging methods (step 34). For example, the MRT contrast particles are substituted by a fluorescent dye with which NIRF examinations can be carried out.

Multiple labeling is also possible, i.e. a contrast agent particle may contain a plurality of contrasting parts for different imaging methods, for example both MR and nuclear medicine labeling, or both MR and fluorescent labeling. Elements which are both MR active and fluoresce, like the lanthanides for example, may alternatively be used as contrasting parts. This allows the patient to be examined by a plurality of imaging methods.

The case may also arise that a plurality of ligands show a good binding affinity to the patient's tissue sample when the CA binding is determined in step 14, for example because they bind to different target structures. In this case, contrast agents which contain a plurality of ligands may be formed for the imaging (step 26) or of the therapy (step 28) of the patient. To this end, a plurality of ligands may be applied on a carrier substance, for example a liposome or an iron oxide particle.

In addition or as an alternative, the ligand may also be used as an "in vitro" diagnostic reagent for consecutive examination, in order to examine further patient samples taken in step 30 (step 32). The samples are preferably blood, i.e. region or stool samples which are easy to take, so long as the target structure is detectable in these tissue samples.

The procedure described here may also be used for "in vitro" differential diagnosis.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining suitability of various contrast agents for an imaging examination of a patient, the method comprising:
    taking a tissue sample from the patient;
    dividing the tissue sample into a plurality of individual samples;
    adding a contrast agent, which binds to a particular target structure in the tissue, to each individual sample, the contrast agent being selected from the various contrast agents; and
    examining the individual samples to determine suitability of the various contrast agents for the imaging examination of the patient.

2. The method as claimed in claim 1, wherein the imaging examination an imaging method including at least one of positron emission tomography (PET), single photon emission computed tomography (SPECT), magnetic resonance tomography (MRI), an optical imaging method and an analytical examination method, and
    wherein the contrast agent contains a contrasting part that generates contrast if used in the imaging method.

3. The method as claimed in claim 1, wherein the contrast agent contains a ligand that binds to the particular target structure in the tissue, and a contrasting part that generates contrast if used in the imaging examination.

4. The method as claimed in claim 3, wherein the ligand is a biologically active molecule.

5. The method as claimed in claim 1, wherein the target structure in the tissue sample is at least one of an antigen, an enzyme and a nucleic acid.

6. The method as claimed in claim 1, further comprising:
    incubating the individual samples after adding the contrast agent in order to bind the contrast agent to the target structure, and
    removing any unbound contrast agent before examining the individual samples.

7. The method as claimed in claim 1, further comprising separating any of the contrast agent not bound by the individual samples, before examining the individual samples.

8. The method as claimed in claim 1, wherein the individual samples of at least two or more patients are examined simultaneously.

9. The method as claimed in claim 1, wherein the tissue sample is taken in at least one of a screening examination and an "in vitro" diagnostic preliminary examination.

10. An imaging method, comprising:
    choosing a suitable contrast agent based on the suitability of the various contrast agents determined according to the method of claim 1; and
    performing the imaging examination of the patient using the suitable contrast agent.

11. A treatment method, comprising:
    choosing a suitable contrast agent based on the suitability of the various contrast agents determined according to the method of claim 1; and delivering a pharmaceutical active agent for treatment of the patient using a ligand of the suitable contrast agent as a carrier for the pharmaceutical active agent.

12. A treatment method, comprising:
choosing a suitable contrast agent based on the suitability of the various contrast agents determined according to the method of claim 1; and
delivering a pharmaceutical active agent for treatment of the patient, the pharmaceutical active agent comprising a ligand of the suitable contrast agent.

13. An imaging method, comprising:
choosing a first suitable contrast agent based on the suitability of the various contrast agents determined according to the method of claim 1;
providing a second contrast agent for an imaging examination, the second contrast agent comprising the ligand of the first suitable contrast agent.

14. An imaging method, comprising:
choosing a suitable contrast agent based on the suitability of the various contrast agents determined according to the method of claim 1; and
performing a consecutive examination for the patient using an in vitro diagnostic reagent, the in vitro diagnostic reagent comprising a ligand of the suitable contrast agent.

15. The method as claimed in claim 1, wherein the imaging examination is an imaging method including at least one of positron emission tomography (PET), single photon emission computed tomography (SPECT), magnetic resonance tomography (MRI), near infrared red fluorescence (NIRF) and bioluminescence, and
wherein the contrast agent contains a contrasting part that generates contrast if used in the imaging method.

16. The method as claimed in claim 2, wherein the contrast agent contains a ligand that binds to the particular target structure in the tissue.

17. The method as claimed in claim 15, wherein the contrast agent contains a ligand that binds to the particular target structure in the tissue.

18. The method as claimed in claim 3, wherein the ligand is at least one of a peptide, a nucleic acid, a virus, a liposome and an antibody.

19. The method as claimed in claim 1, further comprising:
selecting a suitable contrast agent, for the imaging examination of the patient, from the determined suitability of the various contrast agents.

20. A method for selection of a suitable contrast agent for carrying out an imaging examination of a patient, the method comprising:
taking a tissue sample from the patient;
dividing the tissue sample into a plurality of individual samples;
adding a contrast agent, which binds to a particular target structure in the tissue, to each individual sample; and
selecting a suitable contrast agent for carrying out the imaging examination of the patient based upon an examination of the individual samples.

21. The method as claimed in claim 20, wherein the imaging examination is an imaging method including at least one of positron emission tomography (PET), single photon emission computed tomography (SPECT), magnetic resonance tomography (MRI), an optical imaging and an analytical examination, and
wherein the contrast agent contains a contrasting part that generates contrast if used in the imaging method.

22. The method as claimed in claim 20, wherein the contrast agent contains a ligand that binds to the particular target structure in the tissue, and a contrasting part that generates contrast if used in the imaging examination.

23. The method as claimed in claim 22, wherein the ligand is a biologically active molecule.

24. The method as claimed in claim 1, wherein examining the individual samples includes performing an imaging method that generates an image for each of the individual samples including the contrast agent, the suitability of the various contrast agents being determined based on the image.

* * * * *